United States Patent [19]

Cook

[11] Patent Number: 5,389,323
[45] Date of Patent: Feb. 14, 1995

[54] METHOD OF FABRICATING A QUASI-ISOTROPIC APPARATUS

[76] Inventor: Richard L. Cook, 444 Lake Mary Rd., Flagstaff, Ariz. 86001

[21] Appl. No.: 116,964

[22] Filed: Sep. 7, 1993

Related U.S. Application Data

[60] Division of Ser. No. 774,701, Oct. 9, 1991, Pat. No. 5,275,598, and a continuation-in-part of Ser. No. 774,701, Oct. 9, 1991.

[51] Int. Cl.⁶ .................... B29C 53/56; B29C 67/14
[52] U.S. Cl. ................... 264/136; 156/191; 156/194; 156/245; 264/155; 264/160; 264/257
[58] Field of Search ........... 156/191, 194, 245, 307.7; 264/257, 258, 154, 155, 156, 136, 160; 606/56

[56] References Cited

U.S. PATENT DOCUMENTS

| | | | |
|---|---|---|---|
| 1,631,668 | 6/1927 | Briggs | 156/191 |
| 2,229,982 | 1/1941 | Mansur et al. | 156/194 |
| 2,594,838 | 4/1952 | Alexander et al. | 264/258 |
| 2,676,823 | 4/1954 | Olson et al. | 264/257 |
| 3,044,922 | 7/1962 | Kappel | 264/258 |
| 4,289,168 | 9/1981 | Lecourt et al. | 156/194 |
| 4,294,639 | 10/1981 | Woelfel et al. | 264/258 |
| 4,519,732 | 5/1985 | Sutcliffe | 264/155 |
| 4,696,711 | 9/1987 | Gresczuk | 264/155 |
| 5,062,844 | 11/1991 | Jamison et al. | 606/56 |

FOREIGN PATENT DOCUMENTS

| | | | |
|---|---|---|---|
| 3628972 | 3/1988 | Germany | 606/56 |
| 3935134 | 4/1991 | Germany | 606/56 |

Primary Examiner—Jay H. Woo
Assistant Examiner—Duane S. Smith
Attorney, Agent, or Firm—H. Gordon Shields

[57] ABSTRACT

A method of forming an Ilizarov ring includes forming two half rings, each of which comprises a length of resin impregnated cloth. Cloth is pre-impregnated with a resin and then wound to provide a plurality of layers in a three dimensional orientation, and then the resin impregnated cloth is placed in a mold. After the resin impregnated cloth is pressed and cured in the mold, the material is removed from the mold and is appropriately machined. Two half rings are secured together to form a single ring.

10 Claims, 2 Drawing Sheets

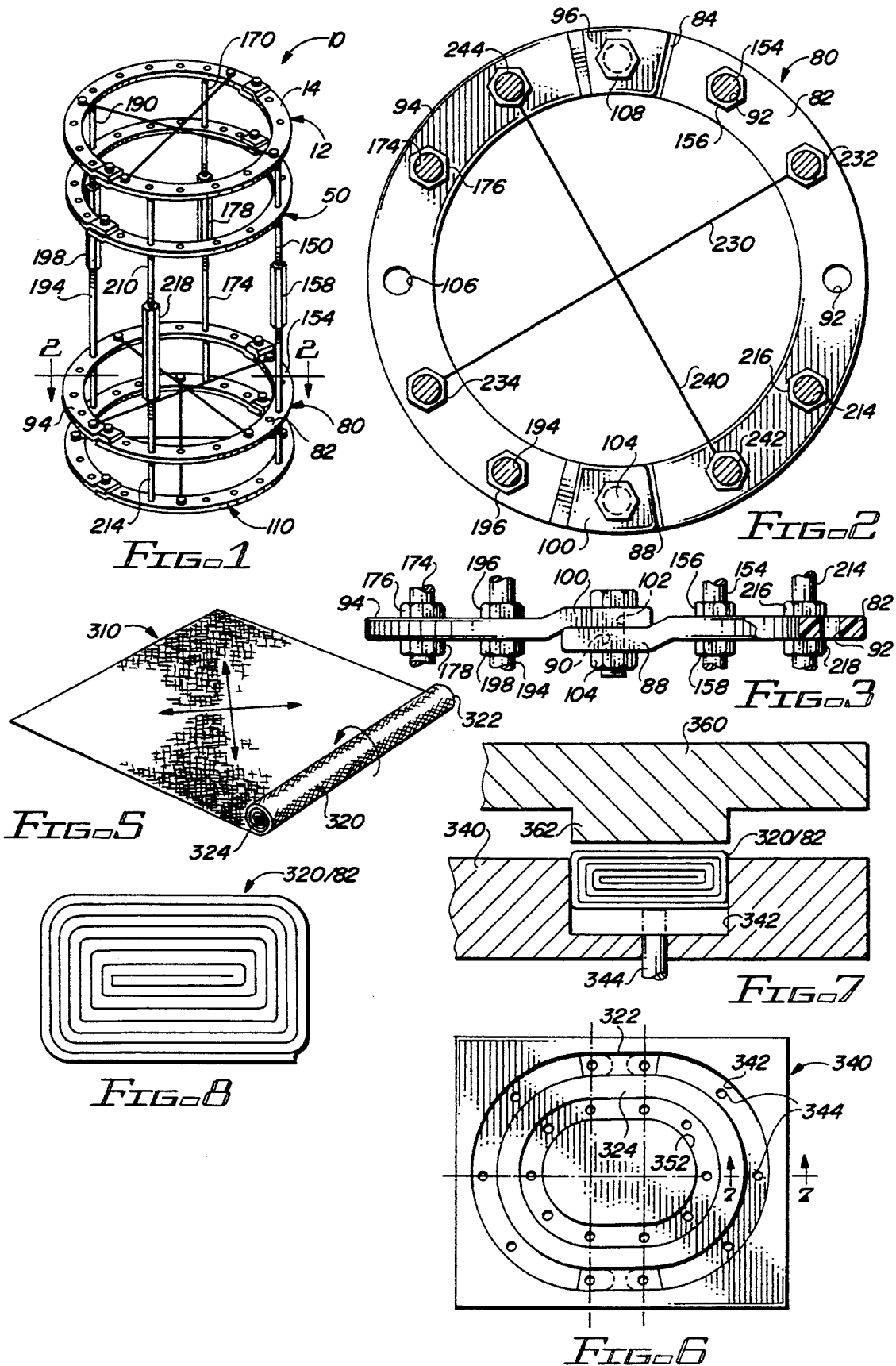

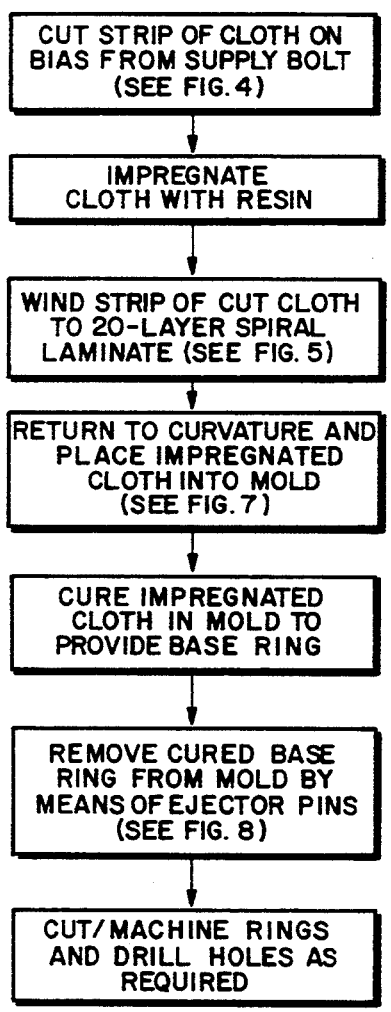
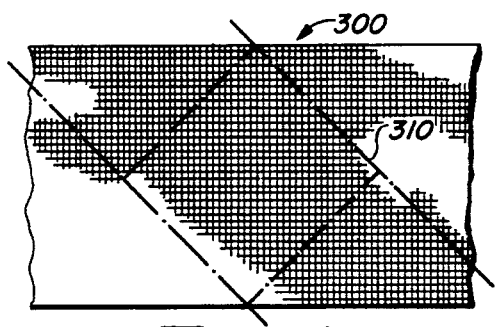
FIG. 4
FIG. 9

METHOD OF FABRICATING A QUASI-ISOTROPIC APPARATUS

CROSS REFERENCE TO RELATED APPLICATION

This application is a divisional and continuation-in-part application of Ser. No. 07/774,701, filed Oct. 9, 1991, now U.S. Pat. No. 5,275,598, dated Jan. 4, 1994.

BACKGROUND OF THE INVENTION

1. Field of Invention

This invention relates to three dimensional laminated quasi-isotropic structures and, more particularly, to a method of fabricating such structure to comprise Ilizarov rings.

2. Description of the Prior Art

Ilizarov rings of the prior art are fabricated of stainless steel. The stainless steel is heavy and opaque to x-rays. In an effort to impart x-ray transparency, while reducing the weight of the rings, and retaining the strength of steel, thus making the rings more comfortable, a graphite and epoxy ring was developed.

The first attempt at this, comprising multiple layers of resin impregnated cloth laminated in flatwise, or two dimensional orientation, lacked the strength necessary to compete with the steel rings. The invention described herein substantially eliminates the problems of both the stainless steel and the two dimensional cloth laminate rings.

Ilizarov rings are secured to body appendages, such as arms or legs, for the purpose of lengthening and reshaping the bones of the appendage. The rings are secured to the body and are spaced apart at a predetermined distance. Periodically the distance between the rings is increased, and the bone to which they are secured is lengthened and/or reshaped over a period of time.

The term "Ilizarov" is named after a Russian doctor who was the inventor of the ring apparatus and of the process for lengthening and reshaping bones.

SUMMARY OF THE INVENTION

The invention described and claimed herein comprises a quasi-isotropic apparatus and a method of fabricating such apparatus into Ilizarov rings and which apparatus equals the strength of steel. The method includes pre-impregnating cloth, such as graphite cloth, with a resin, such as epoxy, cutting the cloth into a bias oriented rectangular strip, and then winding the cloth strip into a spiral to provide a multi-layered cylindrical structure. The resin impregnated material is reshaped to the curvature of a mold, and is then placed in the mold and pressed. As the pressure increases, the spiral structure expands to the shape of the mold. Ejector pins of the mold are aligned with the locations at which holes will be drilled in the finished rings. The resin impregnated cloth winding is then cured in the mold. After curing, the ring is removed from the mold and is appropriately machined. The rings are molded as two half rings, and the half rings are secured together in their use environment. Rings of different sizes are molded so as to fit reasonably closely to the particular anatomy or appendage to which they are secured.

Among the object of the present invention are the following:

To provide new and useful method of manufacturing an Ilizarov ring;

To provide new and useful three dimensional quasi-isotropic apparatus from a multi-layer spiral wound cloth laminate;

To provide new and useful method of using cloth impregnated with a resin;

To provide new and useful three dimensional structure by creating a multiple ply box-beam from a spirally wound impregnated cloth strip;

To provide new and useful method of fabricating a resin impregnated cloth winding into a ring; and To provide new and useful method of forming a ring by simultaneously forming two half rings which subsequently appropriately mate together to form a single ring.

BRIEF DESCRIPTION OF THE DRAWING

FIG. 1 is a perspective view of apparatus embodying the present invention.

FIG. 2 is a plan view taken generally along line 2—2 of FIG. 1.

FIG. 3 is a side view in partial section through a portion of the apparatus of the present invention.

FIG. 4 is a perspective illustrating a portion of the method of the present invention.

FIG. 5 is a perspective view illustrating a portion of the method of the present invention sequentially following FIG. 4.

FIG. 6 is a plan view of a mold used in the practice of the present invention.

FIG. 7 is a view in partial section of a portion of the apparatus of the present invention taken generally along line 7—7 of FIG. 6.

FIG. 8 is a schematic illustration through a completed apparatus embodying the present invention.

FIG. 9 is a block diagram illustrating the method of the present invention.

DESCRIPTION OF THE PREFERRED EMBODIMENT

FIG. 1 is a perspective view of an Ilizarov ring assembly 10. The ring assembly 10 includes four separate ring structures or elements 12, 50, 80, and 110, with the ring elements being paired and spaced apart from each other. That is, there are two pairs of rings, including a pair of rings 12 and 50 and a pair of rings 80 and 110. The rings in each pair are spaced apart from each other, and the two pairs of rings are spaced apart from each other a greater distance.

The paired rings 12 and 50 are spaced apart from each other, and the paired rings 80 and 110 are spaced apart from each other. The pairs of rings 12, 50 and 80, 110 are spaced apart from each other a greater distance than the rings of each pair. The rings 12, 50, 80, 130 are all parallel to each other. The lengthening or reshaping of a limb or appendage occurs between the pairs of rings, or between the rings 12, 50 and the rings 80, 130.

The four rings 12, 50, 80, and 110 are typically coupled together by four pairs of tie rods, with each pair of rods being aligned with each other and secured together by a turnbuckle. The rods are appropriately secured to the rings, and the turnbuckles are used to force the two pairs apart, thus increasing the distance between the pairs of rings. In this manner, the bone or appendage about which the rings are disposed and to which the rings are secured is lengthened or reshaped.

While four pairs of rods, or tie rods, are shown secured to the rings, there is a plurality of holes or apertures extending through the rings that is greater than merely four. The other holes or apertures are used to secure wires to them, and the wires in turn extend through the limb of the user and through the bone of the user to secure the rings to the user. The wires extend diametrically across the rings and through the user's bone.

It will be noted that two pairs of rings are secured to the user's limb and to each other for purposes of stability. That is, the two pairs of rings provide stability with respect to the users limb to prevent an asymmetrical orientation or movement of the rings with respect to the limb or appendage to which the rings are secured.

Each ring is made of two portions, with the portions over-lapping to define a complete, 360 degree, ring.

FIG. 2 is a top or plan view of the ring 80 taken generally along 2—2 of FIG. 1. FIG. 3 is a side view in partial section of the ring of FIG. 2. For the following discussion, reference will primarily be made to FIGS. 1, 2, and 3.

The ring 12 includes a half ring 14 and a half ring 26. Each half ring includes an offset portion at each end, and the offset portions are appropriately mated together and secured by a nut and bolt assembly. The ring 50 similarly includes two half rings, a half ring 52 and a half ring 64. Again, each half ring includes a offset portion, with apertures extending through the offset portions, and the offset portions are aligned and secured together by nut and bolt assemblies.

In addition to the apertures in the offset portions, which are used to secure the half rings together, each half ring also includes a plurality of apertures extending through the half ring. The apertures are spaced apart from each other and are appropriately diametrically aligned with apertures of the mating half ring. The apertures which extend through the half rings are used to secure wires which extend through the user's limb and bone for purposes of securing the rings to the user, and also to secure the tie rods together. It is the tie rods that tie together the four rings which comprise the ring assembly 10. It is also the tie rods, as discussed above, which are used to lengthen the distance between the pairs of half rings to lengthen the bone and the limb.

The rings 80 and 110 are substantially identical to the rings 12 and 50. That is, the rings 80 and 110 each include two half rings, with the half rings secured together at offset portions. The rings 80 and 110 each include apertures extending through their half rings. In use, all of the apertures are appropriately aligned with each other, and the rings are generally parallel to each other.

The ring 80 is illustrated in detail in FIGS. 2 and 3. FIG. 2 comprises a top, plan view of the ring 80, and FIG. 3 comprises a side view of the ring 80. For the following discussion of the ring 80, which is typical of all the rings, attention will be directed primarily to FIGS. 2 and 3.

The ring 80 comprises a three dimensional quasi-isotropic laminated ring which includes a half ring 82 and a half ring 94. The half ring 82 includes an offset portion 84 and an offset portion 88. The offset portions each include apertures extending through them, and an aperture 90 in the offset portion 88 is illustrated in FIG. 3.

A plurality of apertures 92 also extend through the ring half 82.

The ring half 94 is substantially identical to the half ring 82, and comprises a mirror image of the ring half 82. The ring half 94 includes an offset portion 96 and an offset portion 100. Again, the offset portions include apertures extending through them. An aperture 102 in the offset portion 100 is shown in FIG. 3. The aperture 102 is aligned with the aperture 90, and a nut and bolt assembly 104 extends through the aligned apertures to secure the offset portions 88 and 100 together, and accordingly to help secure the ring halves 82 and 94 together.

In the offset portions 84 and 96, a nut and bolt assembly 108 is used to secure the offset portions together. The ring halves 82 and 94 are accordingly secured together at their respective and aligned offset portions by the nut and bolt assemblies 104 and 108.

As best understood from FIG. 3, the ring halves 82 and 94 are appropriately aligned with each other in a common plane. The alignment is, of course, provided by the offset portions at the outer ends of each ring half.

Returning again to FIG. 1, there are four pairs of tie rods shown. There is a tie rod 150 and a tie rod 154 secured together by a turnbuckle 160. The tie rod 150 is appropriately secured to the rings 12 and 50 by nuts. The nuts have been omitted from FIG. 1 for all of the tie rods for purposes of clarity. However, nuts for securing the tie rods to the ring 80 are shown in FIGS. 2 and 3. The securing of the tie rods to the rings is well known and understood. The tie rod 154 is appropriately secured to the rings 180 and 110. The turnbuckle 160 is secured to the "inner" ends of the tie rods 150 and 154. The ends of the tie rods 150 and 154 disposed in the turnbuckle 160 are appropriately oppositely threaded so that rotation of the turnbuckle 160 in one direction will cause the tie rods 150 and 154, and consequently the rings, to move or extend away from each other, and rotation of the turnbuckle 160 in the opposite direction cause the tie rods and the rings to which they are secured, to move towards each other. This is, of course, well known and understood in the art.

A second pair of tie rods 170 and 174 is secured together by a turnbuckle 180. The tie rod 170 is appropriately secured to the rings 12 and 50, and the tie rod 174 is appropriately secured to the rings 80 and 110.

A third pair of tie rods 190 and 194 is secured together by a turnbuckle 200. The tie rod 190 is secured to the ring 12 and the ring 50, and the tie rod 194 is secured to the ring 80 and the ring 110.

A fourth pair of tie rods 210 and 214 is secured together by a turnbuckle 220. The tie rod 210 is appropriately secured to the rings 12 and 50, and the tie rod 214 is appropriately secured to the ring 80 and the ring 110.

The tie rod pairs are appropriately symmetrically located or spaced apart with respect to each other. For lengthening or increasing the distance between the ring pairs 12, 50 and 80, 110, all four of the turnbuckles 160, 180, 2008, and 220 are appropriately rotated the same direction substantially the same amount. A lengthening of the limb to which the rings are secured is accordingly and thusly accomplished over a period of time.

In FIG. 2 a nut 158 shown secured to the rod 154, and a nut 176 is shown secured to the rod 174. A nut 196 is shown secured to the rod 194, and a nut 216 is shown secured to the rod 214. The nuts 156, 176, 196, and 216 are each one of a pair of nuts disposed on opposite sides of the ring 80 for securing the tie rods 154, 174, 194, and 214, respectively, to the ring 80. This is typical of the securing of the tie rods to the rings of the apparatus 10, and is well known and understood in the art. The other nuts 158, 178, 198, and 218 are shown in FIG. 3.

For securing the rings to a limb, wires extend through the limb and are secured to the rings. In FIG. 2, two such wires 230 and 240 are shown. The wire 230 extends between a pin and nut assembly 232 on the ring half 82 and a pin and nut assembly 234 on the ring half 94. The pin and nut assemblies 232 and 234 are used to secure the wire 230 to the ring 80.

The second wire 240 is secured to the ring half 82 by a pin and nut assembly 242, and by a pin and nut assembly 244 to the ring half 94. The pin and nut assemblies 232 and 242, the tie rods 154 and 214, are appropriately extended through and are secured to the apertures 92 in the ring half 82. The pin and nut assemblies 234 and 244 and the tie rods 174 and 194 extend through and are appropriately secured to the apertures 106 and the ring half 94.

For convenience, only the tie rods 154, 214, and 174, 194 are illustrated in FIG. 3. The nuts securing the rods to the ring 80 are shown in FIG. 3. The pin and nut assemblies for the wires 230 and 240 are not shown in FIG. 3.

Each of the Ilizarov rings 12, 50, 80 and 110 comprise two halves, made of ring halves, as discussed above. However, in fabrication, the rings are actually formed from oval elements, each of which comprises a multiple ply box-beam, also referred to as a three dimensional quasi-isotropic laminate comprised or made from a spirally wound impregnated cloth. See FIG. 8.

Cloth, preferably graphite cloth, is impregnated with a thermosetting resin, such as epoxy. The cloth is cut on a bias into a rectangle. This is illustrated in FIG. 4. FIG. 4 is a perspective view of cloth 300 being cut on a bias to provide a cloth rectangle 310. As is well known and understood, the bias of a woven cloth is diagonal to the warp and woof of the weave.

A strip of cloth 310 is shown in FIG. 5 being spirally wound. FIG. 5 is a perspective view of the strip of cloth 310 partially wound into a multiple layered spiral laminate 320.

The strip of cloth 310 is then spirally wound as the precurser to form a multi-layered laminate 320. The spiral wound laminate 320 preferably includes about 20 layers of the cloth 310.

The primary reason for cutting the cloth rectangle 310 on the bias is to eliminate fiber stresses in the spiral wound laminate 320 as it is reshaped to fit the curvature in a mold. A lower mold 340 is shown in FIG. 6.

In FIG. 5, the spirally wound laminate 320 is shown in a round or spiral cylindrical cross-sectional configuration. In FIGS. 3 and 8, the cross-sectional configuration of the cured laminate is shown as generally rectangular. This configuration is assumed in the mold during the curing process, as will be discussed below.

FIG. 6 comprises a top view of a mold 340 in which there are two oval cavities 342 and 352. The cavities 342 and 352 are generally concentrically disposed with respect to each other. Since rings of different sizes are required, the two cavities 342 and 352 accommodate spiral wound lamanites of different sizes.

The spiral wound cloth laminate 320 has two ends, an end 322 and an end 324. The spiral wound laminate 320 will be disposed in the cavity 342 with its ends 322 and 324 disposed adjacent to each other. The ends 322 and 324 are placed in the area of the cavity 342 that will comprise the ends of adjacent half rings, or the area between what will be the outer ends of adjacent offset portions of the half rings.

The reason for the oval orientation of the cavities 342 and 352 is, of course, to accommodate the irregular end portions of the ring halves which will eventually be cut off as scrap. The center line of the ring halves is illustrated in FIG. 6, along with the diameter areas of the offset portions of the ring halves.

FIG. 7 is a side view in partial section through a portion of the cured spirally wound laminated box-beam 320/ring half 82 element being ejected from the mold. Above the cured element 320/82 is a portion of an upper mold 360 and a cavity element 362. An ejector pin 344 extends upwardly through the cavity 342 of the bottom mold 340. The ejector pin 344 remains flush with the bottom of the mold cavity 342 during the curing process.

The use of ejector pins such as the pin 344 is well known and understood in the art. The ejector pins are precisely placed on the hole locations, later to be drilled in the box-beam rings. This is to eradicate surface imperfections caused by the ejector pins.

FIG. 8 is a cross sectional view schematically illustrating the box-beam multi-layered structure of a completed three dimensional quasi-isotropic laminate 320/82. The cross sectional configuration of the original spiral windings is now generally a spiral rectangle. The three dimensional quasi-isotropic properties may be understood from the spiral multi-layer configuration.

FIG. 9 comprises a block diagram of the steps of preparing an Ilizarov ring according to the present invention. Sequentially, a bolt of cloth or fabric or segment thereof is impregnated with a thermosetting resin of some type, such as an epoxy resin. A rectangular strip or piece of cloth is cut on the bias from the pre-impregnated cloth. The bias cut impregnated cloth is then wound to provide a spirally wound roll having about twenty layers. If desired, of course, a pre-impregnated cloth may also be used. Typically, cloth made of graphite fibers is used.

The wound cloth is appropriately curved and placed in a mold. The mold, of course, comprises two parts, and the two parts are brought together to provide appropriate pressure on the spirally wound cloth roll. As pressure is applied, the round shape of the spiral winding expands outwardly to assume the rectangular cross-section of the mold, thus forming the sought after or desired three dimensional box-beam structure shown in FIGS. 3, 7, and 8.

Heat is applied during the curing process. After the appropriate amount of time during which the heat and pressure are applied to the mold, the mold halves are separated and the cured ring elements are ejected from the mold. As indicated above, the ejector pins in the mold are disposed in the areas at which the apertures will be drilled.

After the cured oval ring has been removed from the mold, it is appropriately cut and drilled. The machining includes separating the two ends to provide the half rings and drilling the holes or apertures through the half rings. A standard tumbler device is used to remove all flashing, residual to the molding process. The machined rings are then ready to be used on a patient or user as needed.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. The method of fabricating an Ilizarov ring, comprising, in combination, the steps of:

providing a length of woven cloth having a warp, a woof, and a bias;

impregnating the length of cloth with a thermosetting resin;

cutting a rectangular strip from the impregnated cloth;

winding the impregnated strip of cloth to provide a multi-layered spiral laminate;

providing a mold having a cavity of a desired configuration;

forming the multi-layered cloth laminate into the configuration of the mold cavity wherein a multi-layered spiral box beam is formed;

placing the laminate in the mold cavity;

curing the cloth laminate in the mold cavity;

removing the cured laminate from the mold cavity; and machining the cured laminate to provide an Ilizarov ring.

2. The method of claim 1 in which the step of cutting the strip includes a step of cutting the cloth on the bias.

3. The method of claim 1 in which the step of machining the cured cloth ring includes the step of drilling a plurality of apertures through the cured laminate.

4. The method of claim 3 in which the step of providing a mold includes the step of placing ejector pins in the mold at desired locations where the apertures will be drilled through the cured laminate.

5. The method of claim 1 in which the step of winding the impregnated cloth comprises the step of providing about twenty layers of cloth in the spiral laminate.

6. The method of claim 1 in which the step of curing the laminate in the mold includes the step of the laminate assuming a generally rectangular cross-sectional configuration.

7. The method of claim 6 in which the step of the laminate assuming a generally rectangular cross-sectional configuration includes the step of applying heat and pressure.

8. A method of making a three dimensional quasi-isotropic laminated structure, comprising, in combination, the steps of:

providing a length of woven cloth having a warp, a woof, and a bias;

impregnating the cloth with a resin;

winding the impregnated cloth to provide a laminate having a spiral crossectional configuration;

providing a mold having a cavity of a desired configuration wherein a spiral box beam laminate is formed;

placing the laminate in the cavity;

curing the laminate in the mold; and removing the cured laminate from the mold.

9. The method of claim 8 in which the step of winding the impregnated cloth includes the step of cutting the impregnated cloth on the bias to provide a rectangular strip.

10. The method of claim 9 in which the step of curing the laminate in the mold includes the step of the laminate assuming a generally rectangular configuration to define a three dimensional quasi-isotropic laminated structure.

* * * * *